(12) United States Patent
Haham Hay (10) Patent No.: US 10,867,733 B2
(45) Date of Patent: Dec. 15, 2020

(54) LIGHTWEIGHT ASYMMETRIC MAGNET ARRAYS WITH MIXED-PHASE MAGNET RINGS

(71) Applicant: EPSITAU LTD., Ariel (IL)

(72) Inventor: Noam Haham Hay, Ariel (IL)

(73) Assignee: EPSITAU LTD., Tel Aviv (IL)

( * ) Notice: Subject to any disclaimer, the term of this patent is extended or adjusted under 35 U.S.C. 154(b) by 0 days.

(21) Appl. No.: 16/679,208

(22) Filed: Nov. 10, 2019

(65) Prior Publication Data

US 2020/0176163 A1 Jun. 4, 2020

Related U.S. Application Data

(60) Provisional application No. 62/772,638, filed on Nov. 29, 2018, provisional application No. 62/780,272, filed on Dec. 16, 2018.

(51) Int. Cl.
*G01R 33/383* (2006.01)
*H01F 7/02* (2006.01)

(52) U.S. Cl.
CPC ......... *H01F 7/0273* (2013.01); *G01R 33/383* (2013.01); *H01F 7/0252* (2013.01)

(58) Field of Classification Search
CPC .... H01F 7/0273; H01F 7/0278; H01F 7/0284; G01R 33/383
See application file for complete search history.

(56) References Cited

U.S. PATENT DOCUMENTS

| | | |
|---|---|---|
| 4,998,084 A | 3/1991 | Aff |
| 5,014,032 A | 5/1991 | Aubert |
| 5,028,903 A | 7/1991 | Aubert |
| 5,084,690 A | 1/1992 | Leupold |
| 5,332,971 A | 7/1994 | Aubert |
| 5,574,417 A | 11/1996 | Dorri et al. |
| 5,659,250 A | 8/1997 | Domigan et al. |
| 5,717,333 A | 2/1998 | Frese et al. |
| 5,801,609 A | 9/1998 | Laskaris et al. |
| 5,900,793 A | 5/1999 | Katznelson et al. |

(Continued)

FOREIGN PATENT DOCUMENTS

| | | |
|---|---|---|
| CN | 105390229 A1 | 3/2016 |
| CN | 106710781 B | 3/2018 |

(Continued)

OTHER PUBLICATIONS

International Application # PCT/IB2019/059644 search report dated Feb. 21, 2020.

(Continued)

*Primary Examiner* — Ramon M Barrera
(74) *Attorney, Agent, or Firm* — Kligler & Associates Patent Attorneys Ltd (57) ABSTRACT

A magnet array includes multiple magnet rings and a frame. The multiple magnet rings are positioned along a longitudinal axis and coaxially with the longitudinal axis, wherein at least two of the magnet rings include mixed-phase magnet rings that are phase-dissimilar. The multiple magnet rings are configured to jointly generate a magnetic field along a direction parallel to the longitudinal axis of at least a given level of uniformity inside a predefined inner volume. The frame is configured to fixedly hold the multiple magnet rings in place.

28 Claims, 4 Drawing Sheets

(56) References Cited

U.S. PATENT DOCUMENTS

| | | |
|---|---|---|
| 6,157,278 A | 12/2000 | Katznelson et al. |
| 6,163,240 A | 12/2000 | Zuk et al. |
| 6,281,775 B1 | 8/2001 | Rapoport |
| 6,317,618 B1 | 11/2001 | Livni et al. |
| 6,333,630 B1 | 12/2001 | Holsinger et al. |
| 6,411,187 B1 | 6/2002 | Rotem et al. |
| 6,489,872 B1 | 12/2002 | Fukushima et al. |
| 6,518,867 B2 | 2/2003 | Laskaris et al. |
| 6,534,984 B2 | 3/2003 | Westphal |
| 7,365,623 B2 | 4/2008 | Xia |
| 7,423,431 B2 | 9/2008 | Amm et al. |
| 7,495,441 B2 | 2/2009 | Amor et al. |
| 7,646,274 B2 | 1/2010 | Rapoport |
| 7,898,257 B2 | 3/2011 | Katznelson |
| 8,358,190 B1 | 1/2013 | Hoff et al. |
| 8,604,794 B2 | 12/2013 | Rapoport |
| 8,773,230 B2 | 7/2014 | Sakellariou et al. |
| 8,798,715 B2 | 8/2014 | Rapoport |
| 9,128,167 B2 | 9/2015 | Sakellariou et al. |
| 9,297,874 B2 | 3/2016 | Rapoport |
| 9,482,643 B2 | 11/2016 | Rapoport et al. |
| 9,562,956 B2 | 2/2017 | Rapoport |
| 9,770,188 B2 | 9/2017 | Rapoport et al. |
| 9,952,294 B2 | 4/2018 | Leskowitz |
| 10,018,694 B2 * | 7/2018 | Vidarsson ............ G01R 33/383 |
| 10,076,266 B2 | 9/2018 | Rapoport et al. |
| 10,426,376 B2 | 10/2019 | Rapoport |
| 2002/0097122 A1 | 7/2002 | Rapoport |
| 2011/0234347 A1 | 9/2011 | Rapoport |
| 2012/0013338 A1 | 1/2012 | Sakellariou et al. |
| 2013/0193973 A1 | 8/2013 | Aubert |
| 2014/0111202 A1 | 4/2014 | Wald et al. |
| 2014/0128725 A1 | 5/2014 | Rapoport |
| 2015/0208994 A1 | 7/2015 | Rapoport |
| 2015/0285882 A1 | 10/2015 | Mezrich et al. |
| 2015/0335261 A1 | 11/2015 | Rapoport |
| 2017/0188879 A1 | 7/2017 | Rapoport |
| 2017/0276747 A1 | 9/2017 | Hugon et al. |
| 2017/0300622 A1 | 10/2017 | Laviolette |
| 2018/0313920 A1 | 11/2018 | Sotgiu |

FOREIGN PATENT DOCUMENTS

| | | |
|---|---|---|
| DE | 202012104183 U1 | 2/2013 |
| DE | 202013101097 U1 | 3/2013 |
| DE | 202013103969 U1 | 9/2013 |
| DE | 202013105276 U1 | 12/2013 |
| EP | 1893986 A1 | 3/2008 |
| EP | 2762927 A1 | 8/2014 |
| EP | 2837948 A1 | 2/2015 |
| EP | 2840409 A1 | 2/2015 |
| EP | 3066499 A1 | 9/2016 |
| EP | 3068297 A2 | 9/2016 |
| WO | 2007120057 A1 | 10/2007 |
| WO | 2010122551 A1 | 10/2010 |
| WO | 2011023913 A1 | 3/2011 |
| WO | 201575709 A2 | 5/2015 |
| WO | 2017134635 A1 | 8/2017 |
| WO | 2017165801 A1 | 9/2017 |
| WO | 201842428 A1 | 3/2018 |

OTHER PUBLICATIONS

International Application # PCT/IB2019/059645 search report dated Feb. 21, 2020.

International Application # PCT/IB2019/059646 search report dated Feb. 21, 2020.

U.S. Appl. No. 16/679,207 office action dated Mar. 19, 2020.

Ren et al., "An Aubert Ring Aggregate Magnet Helmet for 3D Head Imaging in a Low-field Portable MRI", Proceedings of the International Society for Magnetic Resonance in Medicine, ISMRM, 27 Annual Meeting and Exhibition, No. 1545, pp. 1-3, May 11-16, 2019.

Ren et al., "Magnet Array for a Portable Magnetic Resonance Imaging System", IEEE MTT-S International Microwave Workshop Series on RF and Wireless Technologies for Biomedical and Healthcare Applications (IMWS-BIO), pp. 92-95, Sep. 21-23, 2015.

Vogel et al., "Rotatable Small Permanent Magnet Array for Ultra-Low Field Nuclear Magnetic Resonance Instrumentation", PLOS ONE, pp. 1-24, Jun. 6, 2016.

Haham Hay et al., U.S. Appl. No. 16/679,207 filed Nov. 10, 2019.

Haham Hay et al., U.S. Appl. No. 16/679,209 filed Nov. 10, 2019.

Hugon et al., "Design, fabrication and evaluation of a low-cost homogeneous portable permanent magnet for NMR and MRI", C. R. Chimie 13, pp. 388-393, year 2010.

Blümler et al., "Hardware Developments: Halbach Magnet Arrays", New Developments in NMR No. 5, Royal Society of Chemistry, pp. 133-157, year 2016.

Chou et al., "Simple method for the generation of multiple homogeneous field volumes inside the bore of superconducting magnets", Nature Scientific Reports, pp. 1-6, Jul. 17, 2015.

Cooley et al., "Design of Sparse Halbach Magnet Arrays for Portable MRI Using a Genetic Algorithm", IEEE Transactions on Magnetics, vol. 54, No. 1, pp. 1-12, Jan. 2018.

Demas et al., "Compact Magnets for Magnetic Resonance", Wiley Periodicals, Inc, pp. 48-59, year 2009.

Manz et al., "A mobile one-sided NMR sensor with a homogeneous magnetic field: the NMR-MOLE", Journal of Magnetic Resonance, issue 183, pp. 25-31, year 2006.

Ren et al., "Design and Optimization of a Ring-Pair Permanent Magnet Array for Head Imaging in a Low-Field Portable MRI System", IEEE Transactions on Magnetics, pp. 1-8, year 2018.

Sakellariou et al., "Permanent magnet assembly producing a strong tilted homogeneous magnetic field: towards magic angle field spinning NMR and MRI", Magnetic Resonance Chemistry, vol. 48, pp. 903-908, Sep. 30, 2010.

* cited by examiner

LIGHTWEIGHT ASYMMETRIC MAGNET ARRAYS WITH MIXED-PHASE MAGNET RINGS

CROSS-REFERENCE TO RELATED APPLICATIONS

This application claims the benefit of U.S. Provisional Patent Application 62/772,638, filed Nov. 29, 2018, and U.S. Provisional Patent Application 62/780,272, filed Dec. 16, 2018, whose disclosures are incorporated herein by reference.

FIELD OF THE INVENTION

The present invention relates generally to magnet assemblies, and particularly to lightweight magnet assemblies comprising permanent magnets and design methods thereof.

BACKGROUND OF THE INVENTION

Designs of permanent magnet arrays aiming at achieving a strong and uniform magnetic field have been previously reported in the patent literature. For example, U.S. Pat. No. 7,423,431 describes a permanent magnet assembly for an imaging apparatus having a permanent magnet body having a first surface and a stepped second surface which is adapted to face an imaging volume of the imaging apparatus, wherein the stepped second surface contains at least four steps.

As another example, U.S. Pat. No. 6,411,187 describes adjustable hybrid magnetic apparatus for use in medical and other applications includes an electromagnet flux generator for generating a first magnetic field in an imaging volume, and permanent magnet assemblies for generating a second magnetic field superimposed on the first magnetic field for providing a substantially homogenous magnetic field having improved magnitude within the imaging volume. The permanent magnet assemblies may include a plurality of annular or disc like concentric magnets spaced-apart along their axis of symmetry. The hybrid magnetic apparatus may include a high magnetic permeability yoke for increasing the intensity of the magnetic field in the imaging volume of the hybrid magnetic apparatus.

U.S. Pat. No. 10,018,694 describes a magnet assembly for a magnetic resonance imaging (MRI) instrument, the magnet assembly comprising a plurality of magnet segments that are arranged in two or more rings such that the magnet segments are evenly spaced apart from adjacent magnet segments in the same ring, and spaced apart from magnet segments in adjacent rings. According to an embodiment, a plurality of magnet segments is arranged in two or more rings with the magnetization directions of at least some of the magnet segments being unaligned with a plane defined by their respective ring, to provide greater control over the resulting magnetic field profile.

U.S. Pat. No. 5,900,793 describes assemblies consisting of a plurality of annular concentric magnets spaced-apart along their axis of symmetry, and a method for constructing such assemblies using equiangular segments that are permanently magnetized.

SUMMARY OF THE INVENTION

An embodiment of the present invention provides a magnet array including multiple magnet rings and a frame. The multiple magnet rings are positioned along a longitudinal axis and coaxially with the longitudinal axis, wherein at least two of the magnet rings are mixed-phase magnet rings that are phase-dissimilar. The multiple magnet rings are configured to jointly generate a magnetic field along a direction parallel to the longitudinal axis of at least a given level of uniformity inside a predefined inner volume. The frame is configured to fixedly hold the multiple magnet rings in place.

In some embodiments, two of the at least two mixed-phase magnet rings contain only a single permanent magnetic phase with a magnetization vector in a direction different by more than 45 degrees from one another.

In some embodiments, each magnet ring has a rotational symmetry with respect to an in-plane rotation of the magnet ring around the longitudinal axis.

In an embodiment, at least one of the magnet rings encircles the predefined inner volume, wherein a minimal inner radius of the magnet rings positioned on one side of a center of the inner volume along the longitudinal axis is different from the minimal radius of the magnet rings positioned on the other side of the center of inner volume. In another embodiment, the inner volume is an ellipsoid of revolution around the longitudinal axis.

In some embodiments, the magnet rings are arranged with reflectional asymmetry with respect to the longitudinal axis.

In some embodiments, a given magnet ring is made of one of a single solid element and an assembly of discrete magnet segments.

In some embodiments, the magnet ring is pre-magnetized with a respective magnetization direction that maximizes uniformity of the magnetic field inside the inner volume. In other embodiments, the magnet ring is pre-magnetized with a respective magnetization direction that minimizes a fringe field outside the magnet array.

In an embodiment, the discrete magnet segments are electrically insulated from each other. In another embodiment, each of the discrete magnet segments has a shape that is one of a shape of sphere, a cylinder, an ellipsoid and a polygonal prism. In yet another embodiment, the discrete magnet segments are separated of each other by at least one non-magnetic element including a solid, gas or liquid.

In some embodiments, the magnet rings have a shape including one of an ellipse, a circle and a polygon.

In some embodiments, each of the mixed phase rings has a discrete rotational symmetry of at least an order eight.

In an embodiment, the magnet array further includes one or more additional arrays of magnet rings, wherein the magnet rings in the additional arrays are coaxial with respective longitudinal axes that are set at respective angles from the longitudinal axis.

There is additionally provided, in accordance with an embodiment of the present invention, a method for producing a magnet array, the method including positioning multiple magnet rings along a longitudinal axis and coaxially with the longitudinal axis, wherein at least two of the magnet rings are mixed-phase magnet rings that are phase-dissimilar, with the multiple magnet rings configured to jointly generate a magnetic field along a direction parallel to the longitudinal axis of at least a given level of uniformity inside a predefined inner volume. The multiple magnet rings are fixedly held in place using a frame.

The present invention will be more fully understood from the following detailed description of the embodiments thereof, taken together with the drawings in which:

DETAILED DESCRIPTION OF EMBODIMENTS

Overview

Magnetic fields that are strong and uniform are needed in a wide variety of disciplines, spanning medicine, aerospace, electronics, and automotive industries. As an example, magnets used in Magnetic Resonance Imaging (MRI) of the human brain typically provide a magnetic field with a strength of 0.1 to 3 Tesla, which is uniform to several parts per million (ppm) inside an imaging volume of approximately 3000 cubic centimeters, e.g. the interior of a sphere of radius 9 cm. However, such magnets have limited applications due to their considerable size and weight. Moreover, in general with magnet designs, there is a severely limiting trade-off between weight, magnetic field uniformity, and a size of a volume inside which a given uniformity can be achieved.

Embodiments of the present invention that are described hereinafter provide lightweight permanent magnet arrays that generate strong and uniform magnetic fields (e.g., in the range of 0.1 to 1 Tesla). Some of the disclosed magnet arrays are configured for emergency-care brain mobile MRI systems, such as a head MRI system inside an ambulance. Generally, however, the disclosed techniques can be applied in any other suitable system.

In the description herein, using a cylindrical reference frame consisting of longitudinal (Z), radial (r), and azimuthal (θ) coordinates, an inner volume is defined as a volume of an ellipsoid of revolution around the longitudinal axis. Examples of an inner volume are a prolate having its long axis along the longitudinal axis, and an oblate having its short axis along the longitudinal axis. A lateral plane is further defined as any r-θ plane (i.e., a plane orthogonal to the longitudinal z-axis). A particular definition of an inner volume is an imaging volume of an MRI system inside which the magnetic field has at least a given level of uniformity.

In some embodiments of the present invention, a magnet array is provided that comprises a frame, which is configured to hold, fixed in place, multiple magnet rings coaxial with a central longitudinal axis at different positions along the axis, wherein the magnet rings lie in lateral planes with at least one ring encircling an area contained in an inner volume through which the longitudinal axis passes (i.e., the ring intersects the inner volume). In the present description a frame is defined by its mechanical capability to hold the rings in place, and which can be made in various ways, for example, using a yoke or by embedding the rings in a surrounding material (e.g., in epoxy).

The multiple magnet rings are arranged with reflectional asymmetry with respect to the longitudinal axis. In the context of the present disclosure and in the claims, the term "reflectional asymmetry with respect to the longitudinal axis" means that no plane perpendicular to the longitudinal axis is a plane of symmetry for the magnet array. In other words, the magnet array is not symmetric under flipping with respect to the longitudinal axis at any point along the axis. Reflectional asymmetry is also referred to as point asymmetry or mirror-image asymmetry. For brevity, any reference to "asymmetry" of the magnet array in the description below means the reflectional asymmetry defined above.

The multiple magnet rings are configured to jointly generate a magnetic field along a direction parallel to the longitudinal axis of at least a given level of uniformity inside the inner volume. The magnet array has each magnet ring generate a magnetic field having a rotational symmetry (continuous or discrete) with respect to an in-plane rotation of the ring around the longitudinal axis.

In some embodiments, each of the magnet rings of any of the disclosed magnet arrays has a shape comprising one of an ellipse, most commonly a circle, or of a polygon. The magnet rings are each made of either a single solid element or an assembly of discrete magnet segments. The magnet rings are pre-magnetized with a magnetization direction which is designed to maximize the uniformity of the magnetic field inside the inner volume and optionally minimize the safety zone defined by the area around the magnet for which the magnetic field exceeds 5 gauss.

In some embodiments, which are typically configured for head MRI applications, a disclosed asymmetric permanent magnet array can be described as comprising a first magnet assembly, comprising two or more magnet rings having a first inner diameter, and a second magnet assembly, comprising two or more magnet rings having a second inner diameter. The first inner diameter is larger than the maximal lateral diameter of the imaging volume and the second inner diameter is smaller than or equal to the maximal lateral diameter of the imaging volume.

Typically, the magnet rings lie in different longitudinal axis positions. The second magnet assembly is asymmetrically placed relative to the imaging volume. The asymmetric structure of the disclosed magnet array is thus optimized to fit a human head, in which physical access to an inner volume (which is the same as the imaging volume) containing the brain is through the first assembly but not the second. The first and second magnet assemblies are configured to jointly generate a magnetic field parallel to the longitudinal axis of at least a given level of uniformity inside the inner volume.

In some embodiments, the asymmetric magnet array is provided with at least two mixed-phase permanent magnet rings that are phase-dissimilar. In the context of the present invention, a mixed-phase magnet ring (MPMR) is defined as a magnet ring comprising multiple, repeating segments, each of which consisting of two or more phases, at least one of which is comprised of a permanent magnetic material.

A phase is defined as an element characterized by a particular combination of (i) material composition, (ii) geometric shape and relative position within the segment, and (iii) magnetization state. The magnetization state is represented by three components of magnetic moment, $M=(M_r, M_\theta, M_z)$, which are shared by corresponding phases in different segments, in the aforementioned cylindrical reference frame of coordinates. The materials of the various phases may be (but not limited to) permanent magnets, ferromagnetic, ferrimagnetic, paramagnetic, diamagnetic, antiferromagnetic or non-magnetic. The total magnetic field of an MPMR at any point is calculated by superposing the contributions of all phases in the ring which have nonzero values of M.

The phases fill the entire MPMR effective volume, which is defined as the volume of a polygonal annular ring of a minimum cross-sectional area, which just encloses all magnetic phases in the ring. The volumetric ratio of a phase is defined as the ratio of the phase volume to the effective volume of the MPMR.

Two MPMRs are said to be phase-similar if there is a one-to-one correspondence between the phases of the two rings for which (a) the volumetric ratios of corresponding phases are the same, (b) the magnetic permeabilities of corresponding non-permanent magnet phases are the same, and (c) the magnetization vectors of corresponding phases differ at most by a rotation through a constant angle in the r-Z plane common for all phases, and by a constant scaling factor in the magnetization magnitudes common for all phases.

Thus, when two MPMRs are phase-dissimilar, the relative contribution of each individual phase in a given ring to the total magnetic field of that ring is different for the two rings. For example, with the aid of computerized magnetic field simulation tools, the phases of at least two MPMRs which are phase-dissimilar, and the magnetic moment directions of their permanent magnet phases, can be adjusted, or "tuned," so as to optimize the uniformity of the total magnetic field inside an inner volume. These extra degrees of freedom are most advantageous when the array is subject to various geometric constraints (such as position of the rings, radial/axial thickness), which commonly arouse from mechanical r or manufactural limitations.

It will be appreciated that a solid magnet ring piece can be magnetized in an azimuthal repetitive manner so as to create repeating segments, with each segment magnetized with a different magnetization direction and/or strength. In the present context, such a magnet piece will be considered an MPMR where the phases share common material composition but differ in their magnetization states, even though mechanically there is no actual segmentation of the magnet ring. The same holds, for instance, for a solid magnet ring created with different material compositions where the composition changes in an azimuthal repetitive way. In such a case, different magnetic compositions areas will be considered as different phases. The same holds for a solid magnet piece which has its axial thickness and/or radial thickness and/or cross section geometry vary azimuthally in a repetitive way. In this case the ring will be considered an MPMR with phases which differ by their geometry but share a common composition and magnetic state, even though there is no segmentation mechanically.

For a given weight of an asymmetric magnet ring array, using two or more phase-dissimilar MPMRs will result in a level of field uniformity inside the inner volume that is substantially higher than that achieved by the asymmetric array incorporating only one MPMR or several phase-similar MPMRs.

The various types of magnet rings disclosed above are typically made of a strongly ferromagnetic material, such as an alloy of neodymium, iron, and boron (NdFeB), whose Curie temperature is well above the maximum ambient operating temperature. Other material options include ferrites, samarium-cobalt (SmCo) magnets, or any other permanent magnet material. Depending on the design and type of ring, ring segments may have the shape of a sphere, a cylinder, an ellipsoid, or a polygonal prism with shapes such as a cuboid, a wedge, or an angular segment.

The two disclosed techniques to realize magnet arrays (e.g., using an asymmetric geometry, using two or more MPMR rings), separately or combined, enable the use of strong and uniform magnet arrays in applications that specifically require lightweight magnet solutions.

Figure 1:
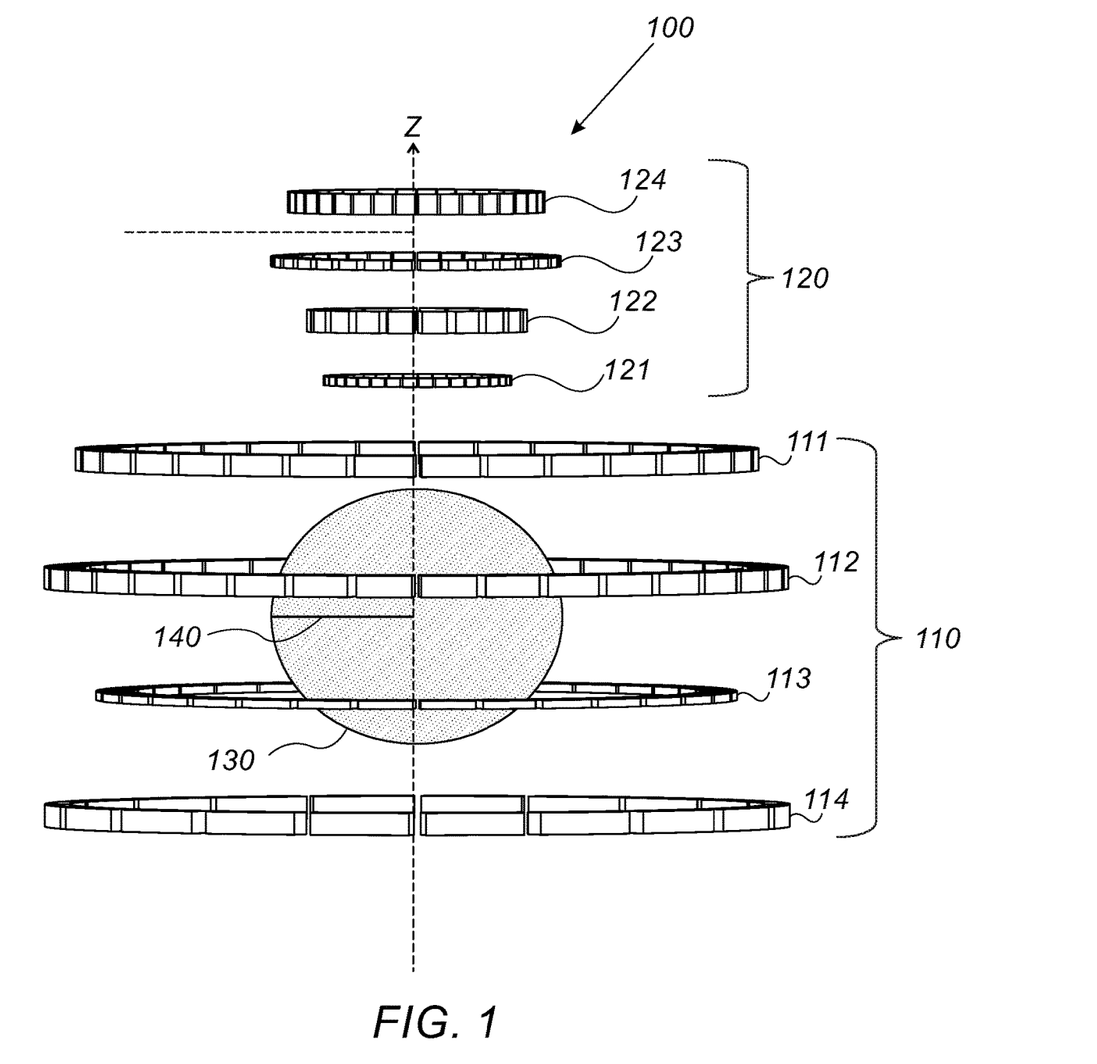
FIG. 1 is a perspective view of an asymmetric magnet array comprising a first magnet assembly and a second magnet assembly, according to an embodiment of the present invention.

FIG. 1 is a perspective view of an exemplary asymmetric magnet array 100 comprising a first magnet assembly 110 and a second magnet assembly 120, according to an embodiment of the present invention. As seen, first and second magnet assemblies 110 and 120 each comprise at least two magnet rings which are coaxial with a central longitudinal axis, denoted "Z-axis," which passes through an inner volume 130. The multiplicity of magnet rings has variable transverse dimensions and variable displacements along the Z-axis. In FIG. 1, by way of example, first assembly 110 is shown as consisting of four magnet rings, 111-114, and second assembly 120 is shown as consisting of four magnet rings, 121-124. Each of the rings in assemblies 110 and 120 is either a solid ring or a segmented ring, i.e., a ring comprising discrete segments. The segments may have the shape of a sphere, a cylinder, an ellipsoid, or a polygonal prism, preferably cuboids. It will be appreciated that the rings may have any cross section including non-regular shape cross section. All segments belonging to a single ring share a common shape and material composition, as well as the same magnetic moment components in the longitudinal (Z), radial, and azimuthal directions. However, one or more of these characteristics may differ from one ring to another.

In case of a segmented ring, referring to the magnetic moment of a segment means that the segment is uniformly magnetized to a specific direction in space, its radial, longitudinal and azimuthal directions are calculated in the segment center of mass.

In case of a solid ring, M varies continuously in space having azimuthal, radial, and longitudinal components independent of the azimuth coordinate. It will be appreciated that a solid magnet piece with a complex shape may be magnetized in a fashion that $M_r$, $M_\theta$, or $M_z$ changes as a function of Z, or R, in a gradual or stepped way, creating effectively several rings from a magnetization perspective, although mechanically composed of one continuous piece. In the present context, this sort of implementation is regarded as having multiple rings where their borders are determined by the magnetization perspective, rather than by mechanical segmentation.

The peripheral shape of the rings may be any closed curve, such as a circle, ellipse, or polygon. In some cases, the choice of peripheral shape depends upon the cross-sectional shape of inner volume 130. It will be appreciated that a rotational symmetry of a ring, implies among others, that its peripheral shape is also rotationally symmetric (For example a shape of a circle, or an equiangular-equilateral polygon). In the special case where all rings are circular, the minimal inner radius of rings 111-114 of first assembly 110 is denoted by R1, and the minimal inner radius of rings 121-124 of second assembly 120 is denoted by R2. For a given target radius Ri, which, by way of example, has the lateral radius 140 of inner volume 130 that defines a maximal radius of a spheroid volume inside that is used for imaging and which the magnetic field has at least a given level of uniformity, the values of R1 and R2 satisfy the relationship Ri<R1, and 0≤R2≤Ri. In the case of R2=0, at least one of the rings of second assembly 120 is a solid disc. It is appreciated that assembly 120 may contain rings with inner radius larger than R2 and even larger than R1. The assemblies are separated in the Z direction with a gap which is typically (but not limited to) 0-10 cm. For the present purpose, if a ring extends in Z direction to both assemblies, one part of the ring will be considered as included in the first assembly while the other part in the second assembly. In this case the gap between arrays will be 0.

In an embodiment, in the asymmetric array, the minimal radius of the rings positioned on one side of the center of the inner volume is different from the minimal radius of the rings positioned on the other side of the center. The center of the inner volume can be defined in any suitable way, e.g., the center of the section of the longitudinal axis that lies within the inner volume. In addition, when the inner imaging volume is only partially enclosed by the array the center will be considered as the center of the section of the longitudinal axis that lies within the inner volume and inside the array. An array which obeys the former embodiment may be described as comprised of two sub-assemblies with different minimal inner radiuses as described above.

Inner volume 130 is a simply-connected region at least partially enclosed by assembly 110, which is typically an ellipsoid or a sphere. As shown, the inner volume 130 is enclosed by the magnet array 110, with rings 112-113 encircling inner volume 130. In an embodiment, inner volume 130 is an oblate ellipsoid with semi-axes approximately equal to 0.5 R1, 0.5 R1, and 0.3 R1. The parameters of such rings are not limited to the inner and outer radius of a ring, its Z displacement, or Z-axis thickness. In addition, magnetic moment angles are all optimized using a calculation method such as a finite element, finite difference, or analytical approach, combined with a gradient descent optimization algorithm to achieve the best uniformity, for a given field strength in the imaging volume, with a minimal weight. This is allowed due to the fact that each assembly contains a multiplicity of rings, all of which are optimized.

One aspect of the asymmetry of magnet array 100 is that different rings have different transverse dimensions and magnetic moment directions wherein the rings are arranged in an array having reflectional asymmetry with respect to the longitudinal axis (i.e., are asymmetrical with respect to Z-axis inversion). In the context of the present disclosure and in the claims, the term "reflectional asymmetry with respect to the longitudinal axis" means that no plane perpendicular to the longitudinal axis is a plane of symmetry for the magnet array. In other words, the magnet array is not symmetric under flipping with respect to the longitudinal axis at any point along the axis. Reflectional asymmetry is also referred to as point asymmetry or mirror-image asymmetry. For brevity, any reference to "asymmetry" of the magnet array in the description below means the reflectional asymmetry defined above.

The asymmetry in the design is particularly advantageous when imaging inherently non-symmetrical specimens, such as the human head. For example, in one such case, it has been found that the rings belonging to assembly 110 may be primarily magnetized in a first given direction (e.g., the r-direction), whereas those belonging to assembly 120 may primarily magnetized in another direction (e.g., the z-direction).

Finally, the direction of magnetization of each individual ring may be optimized to obtain both uniformity in the inner volume as well as fringe field reduction so as to create a magnetic circuit which closes the field lines close to the magnet ring. In an embodiment, the discrete magnet segments are each pre-magnetized with a respective magnetization direction that minimizes a fringe field outside the magnet array.

FIGS. 2A and 2B-2D are a perspective view of an asymmetric magnet array 200, and plots of magnetic field lines generated separately and jointly by the assemblies, respectively, according to another embodiment of the present invention. Uniformity is not evident by uniform density of the lines (as lines were drawn denser in the imaging zone for better details) rather by z-axis alignment of the lines.

Figure 2A:
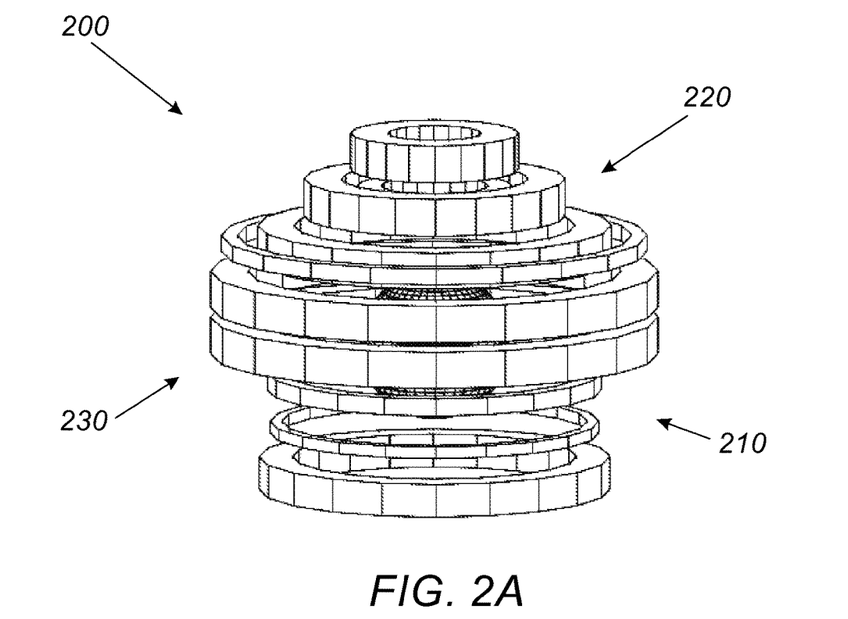
FIGS. 2A and 2B-2D are a perspective view of an asymmetric magnet array, and plots of magnetic field lines generated separately and jointly by the assemblies, respectively, according to another embodiment of the present invention.

As seen in FIG. 2A, an inner volume 230 is a simply-connected region at least partially enclosed by a first magnet assembly 210, which is typically an ellipsoid or a sphere. A second magnet assembly 220 of the asymmetric array, "caps" inner volume 230. As mentioned above, different rings may have different magnetization directions to optimize the uniformity and fringe field of the magnet array. For instance, one ring may have a magnetization vector in a direction substantially different (e.g., by more than 45 degrees) from another ring. For instance, the magnetization vectors of the permanent magnet segments may point primarily in the r direction in one ring, and primarily in the Z direction in another ring. Furthermore, two rings belonging to the same assembly may have substantially different magnetization directions. For instance, one ring of the first assembly may have its magnetization primarily in the r direction, another ring of the first assembly may have its magnetization in primarily the –z direction while a third ring of the first assembly may have its magnetization at –45 degrees in the r-z plane. In an embodiment, the two or more ring have a magnetization vector in a direction different by more than 45 degrees from one another.

In a particular case (not shown) it was found that the rings in assembly 210 are dispersed in their inner radius between 15 cm and 30 cm, and dispersed in their Z position in a length of 25 cm, while the rings in assembly 220 are dispersed in their inner radius between 0.05 cm and 30 cm, and dispersed in their Z position in a length of 12 cm, with the displacement between the two assemblies in the Z direction between 0 cm and 10 cm.

Figure 2B:
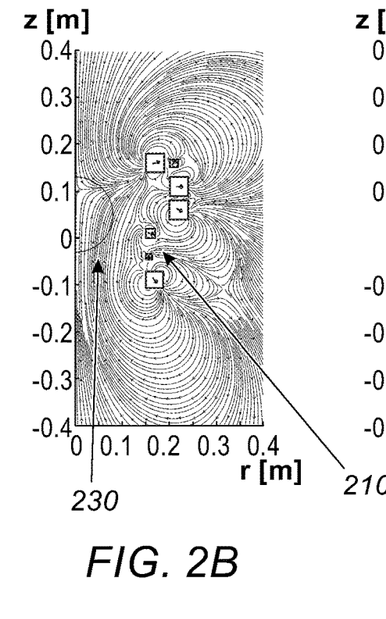

FIG. 2B shows the magnetic field lines of the field generated by first magnet assembly 210 (rings cross-sectionally illustrated by squares, each with a direction of magnetization of the ring in an r-z plane) inside and outside an inner volume 230. As seen, the field lines inside inner volume 230 are largely aligned along the z-axis, however they sharply bend at the top portion of volume 230, where the field becomes exceedingly non-uniform.

Figure 2C:
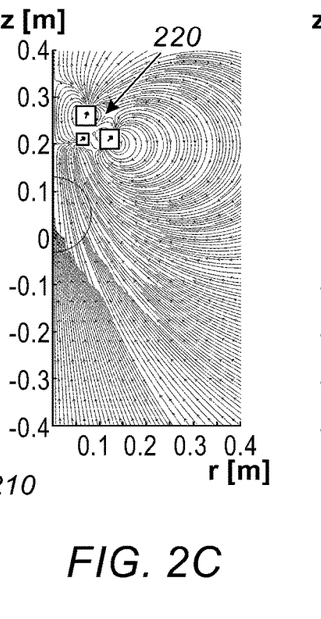

FIG. 2C shows the magnetic field lines of the field generated by second magnet assembly 220 inside and outside an inner volume 230. As also seen here, the field lines inside inner volume 230 are largely aligned along the z-axis. However, they tilt opposite to the field lines of FIG. 2B with respect to the z-axis, and become exceedingly non-uniform at a bottom portion of volume 230.

Figure 2D:
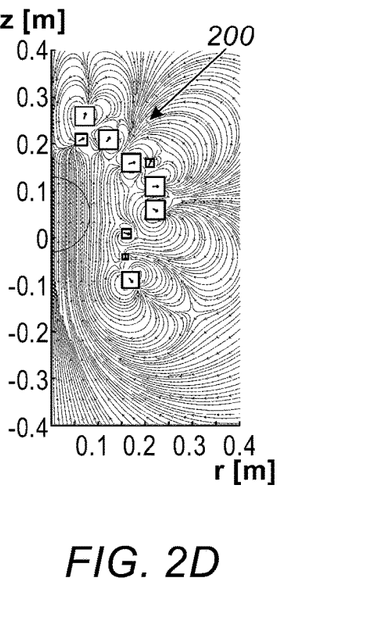

As seen on FIG. 2D, when combined into a full array 200, assemblies 210 and 220 compensate for each other's field non-uniformity, to achieve a uniform magnetic field along the z-axis to a better degree than a prespecified threshold.

FIGS. 2A-2D show an exemplary array containing ten rings. It will be appreciated that the array may contain more rings (e.g., several tens or hundreds of rings) which are all optimized as described above. The more rings contained in the array, the better magnet performance can be achieved (e.g., higher uniformity level, larger magnetic field or larger imaging volume). The improved performance comes with the drawback of increased complexity and production cost of the array due to the large number of elements. Thus, a practitioner skilled in the art should consider the required number of rings according to the specific application.

Figure 3:
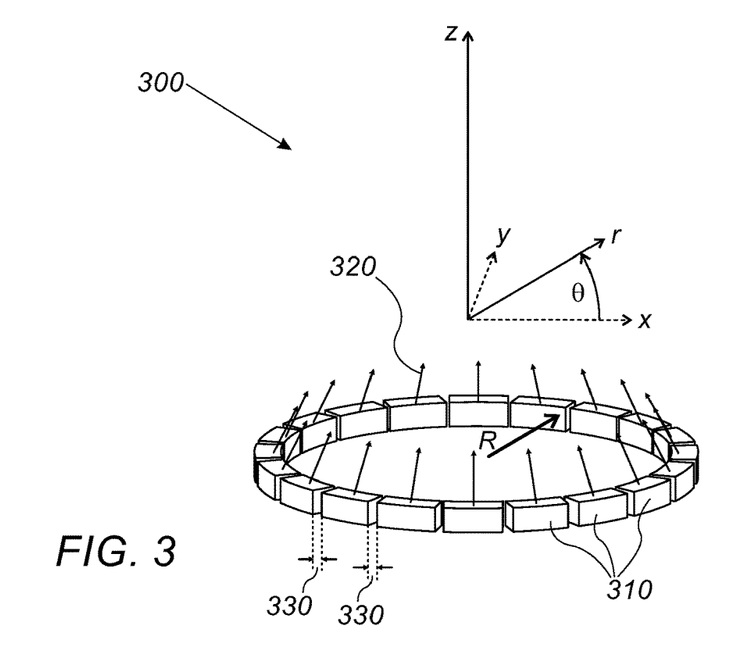
FIG. 3 is a perspective view of a segmented magnet ring, which may be any one of the rings in the magnet arrays of FIGS. 1 and 2, according to an embodiment of the present invention.

FIG. 3 is a perspective view of a single segmented magnet ring 300, which may be any one of the rings in magnet arrays 100 and 200 of FIGS. 1 and 2, according to an embodiment of the present invention. In FIG. 3, each magnet segment 310 has a magnetization vector 320 lying in the r-Z plane, with similar longitudinal (Z) and radial (r) components. Furthermore, each segmented ring possesses rotational symmetry with an azimuthal period equal to 360/N degrees where N is the number of segments in the ring. (For a solid ring, i.e., for N→∞, the rotational symmetry is continuous). In some embodiments, the disclosed rings have rotational symmetry of an order N≥8. It will be appreciated that the disclosed array contains rings with rotational symmetry and hence the result magnetic field is along the longitudinal axis. It is possible however to incorporate in the asymmetric array rings which are non-rotationally symmetric in a fashion that optimizes the fringe field and uniformity in the inner volume. In such a case the magnetic field may be along an arbitrary axis. Although such an array may be substantially worse than a rotationally symmetric array, the use of asymmetry with rings as disclosed may substantially improve uniformity of the array compared to a symmetric one.

Discrete segments 310 are equally spaced and attached to one another using, for example, an adhesive, which is preferably non-electrically conducting, or are held together mechanically with gaps 330 between adjacent segments filled by (but not limited to) a preferably insulating material. It will be appreciated that the rotational symmetric segmented rings may also include a combination of more than one type of segments. For thermal stability of all of ring 300, it is preferable that the adhesive or gaps consist of a material which is also thermally conductive, such as silicon oxide, silicon nitride, or aluminum oxide. Individual magnet segments 310 may be made of the aforementioned strongly ferromagnetic materials, whose Curie temperature is well above the operating temperature of an associated system that includes such elements as an array 200, e.g., a mobile MRI system.

It will be appreciated that the descriptions in FIGS. 1-3 are intended only to serve as examples, and that many other embodiments are possible within the scope of the present invention. For example, rotation of the magnet moment vector in the r-z-e plane can be achieved, in an alternative embodiment, by rotating the individual magnet segments 310 through a distinct angle of rotation, which may be different for different rings. Further, magnet arrays 100 and 200 may be combined with either a static or dynamic shimming system, to further improve field uniformity inside inner volumes 130 and 230, respectively. When dynamic shimming or gradient pulse fields are used, the presence of electrically insulating adhesive or empty gaps between adjacent magnet segments 310 helps to minimize the negative effects of eddy currents on field uniformity. Furthermore, magnet arrays 100 and 200 may be combined with resistive coils placed concentric to the z-axis, in order to enhance the magnetic field strength inside inner volumes 130 and 230.

Magnet Array Including Mixed Phase Magnet Rings

Figure 4:
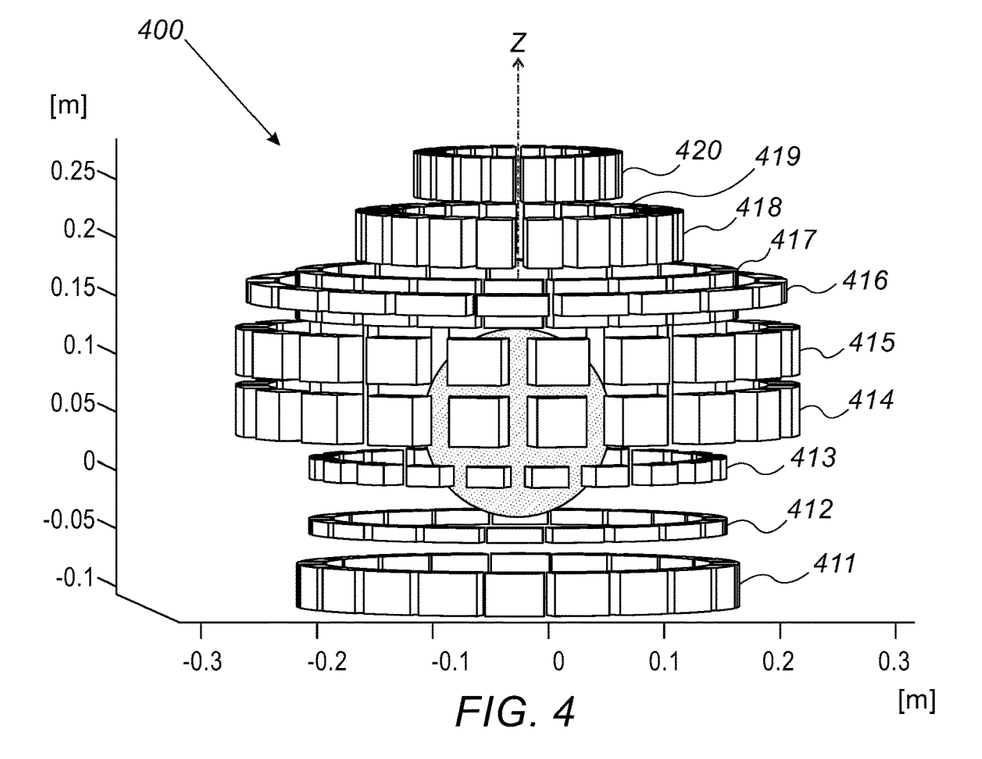
FIG. 4 is a perspective drawing of a magnet array of phase-dissimilar mixed-phase magnet rings (MPMRs), according to an embodiment of the present invention.

FIG. 4 is a perspective drawing of a magnet array 400 of phase-dissimilar mixed phase magnet rings (MPMRs), according to an embodiment of the present invention.

As seen, by way of example, array 400 comprises ten magnet rings 411-420 which are coaxial with a central Z-axis passing through an inner volume 430. The different rings are located at different positions along the Z-axis and, in general, have different transverse dimensions, radial thicknesses, and axial thicknesses. As seen, magnet array 400 has reflectional asymmetry with respect to the longitudinal axis (i.e., is asymmetric with respect to Z-axis inversion). In the context of the present disclosure and in the claims, the term "reflectional asymmetry with respect to the longitudinal axis" means that no plane perpendicular to the longitudinal axis is a plane of symmetry for the magnet array. In other words, the magnet array is not symmetric under flipping with respect to the longitudinal axis at any point along the axis. Reflectional asymmetry is also referred to as point asymmetry or mirror-image asymmetry. For brevity, any reference to "asymmetry" of the magnet array in the description below means the reflectional asymmetry defined above.

In addition, inner volume 430 may be interior (as shown) or at least partially extending exterior in the z-direction (not shown) to magnet array 400. Furthermore, the disclosed magnet array may or may not be combined with a yoke.

Ring 411 exemplifies an MPMR having cuboid-shaped permanent magnet elements (i.e. phase 1) separated by relatively small non-magnetic gaps (i.e. phase 2). Ring 413 exemplifies an MPMR having cuboid shaped permanent magnet elements (i.e. phase 1) separated by relatively large non-magnetic gaps (i.e. phase 2). Clearly, the fraction of the total ring volume occupied by non-magnetic gaps is small in the case of ring 411 and relatively large in the case of ring 413. Thus, rings 411 and 413 are MPMRs that are phase-dissimilar and array 400 may contain many phase-dissimilar MPMRs.

Furthermore, ring 411 may also have a magnetization vector in a direction substantially different (e.g., by more than 45 degrees) from ring 413. For instance, the magnetization vectors of the permanent magnet segments may point in the −Z direction in ring 411, and −45 degrees in the r-Z plane in ring 413. In an embodiment, the two or more mixed-phase magnet rings contain only one magnetic phase with a magnetization vector in a direction different by more than 45 degrees from one another. Each MPMR ring possesses rotational symmetry with an azimuthal period equal to 360/N degrees where N is the number of segments in the ring. (For a continuous ring, i.e., for N→∞, the rotational symmetry is continuous). In some embodiments, the disclosed MPMR rings have discrete rotational symmetry of an order N≥8.

Figure 5:
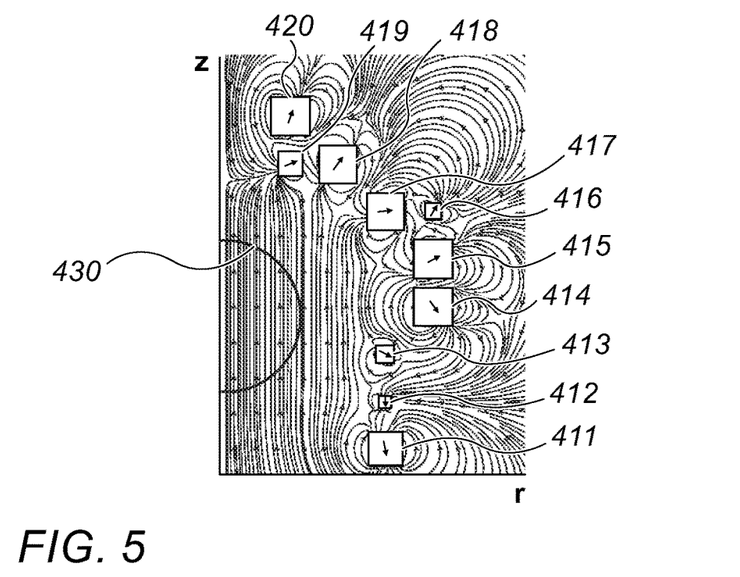
FIG. 5 is a plot of magnetic field lines generated by the magnet array of FIG. 4, according to an embodiment of the present invention.

FIG. 5 is a plot of magnetic field lines generated by magnet array 400 of FIG. 4, according to an embodiment of the present invention. Uniformity is not evident by uniform density of the lines (as lines were drawn denser in the imaging zone for better details) rather by z-axis alignment of the lines. MPMR array 400 can achieve, at a same array weight, a more uniform magnetic field along the z-axis, compared with, for example, that achieved with arrays 100 and 200. Moreover, the uniform field extends radially almost to the rings. Such lightweight MPMR arrays may be therefore particularly useful for mobile MRI applications, such as an MRI ambulance.

FIGS. 4 and 5 show an exemplary array 400 containing ten MPMRs. It will be appreciated that the array may contain more MPMRs (e.g., several tens or hundreds of MPMRs) which are all optimized as described above with many of them phase dissimilar. The more rings contained in the array, the better magnet performance can be achieved (e.g., higher uniformity level, larger magnetic field or larger imaging volume). The improved performance comes with the drawback of increased complexity and production cost of the array due to the large number of elements. Thus, a practitioner skilled in the art should consider the required number of MPMRs according to the specific application.

Figure 6:
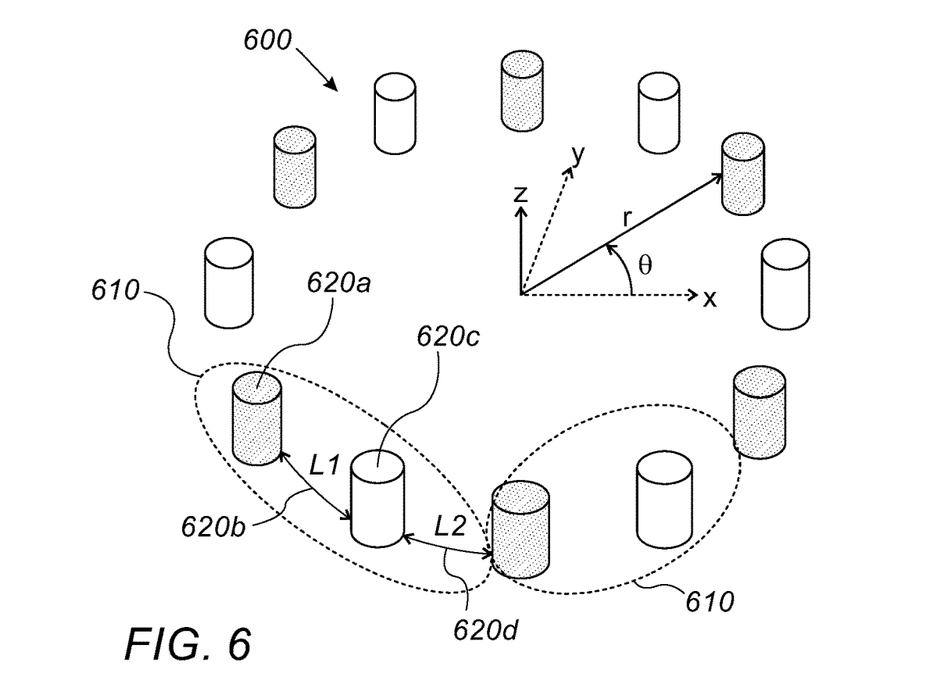
FIG. 6 is a perspective view of a mixed-phase magnet ring (MPMR), which may be any one of the rings in the magnet array of FIG. 4, according to an embodiment of the present invention.

FIG. 6 is a perspective drawing of an exemplary MPMR 600 according to an embodiment of the invention. The ring consists of six repeating segments 610, each of which has four elements: 620a, 620b, 620c, and 620d.

In an embodiment, elements 620a are made of the aforementioned strongly magnetic materials. Elements 620a are typically pre-magnetized with specific values for the components of magnetic moment. The shape of element 620a may be cylindrical, as shown in FIG. 3, or some other shape such as a sphere, an ellipsoid, a cuboid, or a polygonal prism.

Element 620c typically has a different phase from element 620a. For example, it may have the same material composition and geometric shape as element 620a, but differ in one or more components of the magnetic moment, M. Alternatively, element 620c may consist of a non-ferromagnetic material, such as a ferrimagnetic, paramagnetic, or non-magnetic material, in which case the phase of element 620c differs from that of element 620a, by virtue of its different material composition.

Element 620b fills a gap of length L1 separating element 620a from element 620c; similarly, element 620d fills a gap of length L2 separating element 620c from element 620a of the adjacent segment, as shown in FIG. 6. Often, for thermal stability of MPMR 600, it is preferable that elements 620b and 620d consist of non-magnetic, electrically non-conducting materials which are at least moderately thermally conductive, such as silicon oxide, silicon nitride, or aluminum oxide.

In order to further illustrate the concept of phase-similar MPMR's, consider an MPMR 600 in which elements 620a and 620c have axial magnetizations M0 and −M0, respectively. Next, consider a different MPMR 600* (not shown) which is the same as MPMR 600 in all respects, except that elements 620a* and 620c* have radial magnetizations 2M0 and −2M0, respectively. Since MPMR 600 can be transformed into MPMR 600* by a common rotation of the magnetic moment by 90° in the r-Z plane followed by multiplication by a common scale factor of two, the two MPMR's are considered to be phase-similar. For each ring one may define the effective strength of the ring by the magnitude of the volume averaged r-Z projection of magnetization vector divided by the largest magnetization magnitude of all permanent magnet phases. The parameter has a value between 0 and 1; and has the qualitative meaning of how effective a ring produces a magnetic field nearby. When two rings are not phase similar, they may have different relative effective strengths and different contributions to the magnetic field.

Generally, adjacent elements in an MPMR are held together by mechanical means or by adhesives. If the total volume occupied by adhesive layers is small, e.g. less than 1% of the total volume of the ring, then the adhesive layers need not be treated as an additional phase for the purpose of magnetic field calculations. Small adjustments in the segments positions and angles may be carried out to compensate for the segments imperfections and residual inhomogeneity.

It will be appreciated that the above descriptions are intended only to serve as examples, and that many other embodiments are possible within the scope of the present invention. For example, magnet array 400 may be combined with either a static or dynamic shimming system to further improve field uniformity inside inner volume 430. When dynamic shimming or gradient pulse fields are used, the presence of electrically insulating material in the gaps between adjacent magnet elements helps to minimize the deleterious effects of eddy currents on field uniformity. Furthermore, magnet array 400 may be combined with resistive coils placed concentric to the z-axis, in order to enhance the magnetic field strength inside inner volume 430.

In the example embodiments described herein, the mixed-phase rings are part of an asymmetric magnet array. In alternative embodiments, however, mixed-phase rings may be used also in symmetric arrays or any other type of magnet array, with or without a yoke to enhance their uniformity. In addition, the example magnet array described herein contains multiple rings coaxial with a common axis. It is however possible to combine the described array with one or more additional ring arrays for which the rings are coaxial with one or more different axes which are at an angle from the first longitudinal common axis. The combination of arrays jointly create a magnetic field in an arbitrary direction in space. The additional ring arrays may also contain mixed phase rings, those rings however are defined according to their own cylindrical coordinate system with a z' axis defined as their own common coaxiality axis.

It is possible, for example, to have two arrays of rings with respective coaxiality axes that differ by 45 degrees from one another. Each array may contain two or more phase-dissimilar MPMRs and may be optimized to obtain a field substantially uniform in the inner volume along each of the array axis. The combination of the two arrays results in a homogeneous magnetic field in a direction which is between the first and second longitudinal axes.

Although the embodiments described herein mainly address mobile MRI application, the methods and systems described herein can also be used in other applications, such as aerospace applications, that require strong, uniform and lightweight magnets such as scanning electron microscopes (SEM).

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A magnet array, comprising:
multiple magnet rings, which are positioned along a longitudinal axis and coaxially with the longitudinal axis, wherein at least two of the magnet rings comprise mixed-phase magnet rings that are phase-dissimilar, and wherein the magnet rings are arranged with reflectional asymmetry with respect to the longitudinal axis, the multiple magnet rings configured to jointly generate a magnetic field along a direction parallel to the longitudinal axis of at least a given level of uniformity inside a predefined inner volume; and a frame, which is configured to fixedly hold the multiple magnet rings in place.

2. The magnet array according to claim 1, wherein two of the at least two mixed-phase magnet rings contain only a single permanent magnetic phase with a magnetization vector in a direction different by more than 45 degrees from one another.

3. The magnet array according to claim 1, wherein each magnet ring has a rotational symmetry with respect to an in-plane rotation of the magnet ring around the longitudinal axis.

4. The magnet array according to claim 1, wherein at least one of the magnet rings encircles the predefined inner volume, and wherein a minimal inner radius of the magnet rings positioned on one side of a center of the inner volume along the longitudinal axis is different from the minimal inner radius of the magnet rings positioned on the other side of the center of inner volume.

5. The magnet array according to claim 1, wherein the inner volume is an ellipsoid of revolution around the longitudinal axis.

6. The magnet array according to claim 1, wherein a given magnet ring is made of one of a single solid element and an assembly of discrete magnet segments.

7. The magnet array according to claim 6, wherein the magnet ring is pre-magnetized with a respective magnetization direction that maximizes uniformity of the magnetic field inside the inner volume.

8. The magnet array according to claim 6, wherein the magnet ring is pre-magnetized with a respective magnetization direction that minimizes a fringe field outside the magnet array.

9. The magnet array according to claim 6, wherein the discrete magnet segments are electrically insulated from each other.

10. The magnet array according to claim 6, wherein each of the discrete magnet segments has a shape that is one of a shape of sphere, a cylinder, an ellipsoid and a polygonal prism.

11. The magnet array according to claim 6, wherein the discrete magnet segments are separated of each other by at least one non-magnetic element comprising a solid, gas or liquid.

12. The magnet array according to claim 1, wherein each of the magnet rings has a shape comprising one of an ellipse, a circle and a polygon.

13. The magnet array according to claim 1, wherein each of the mixed phase rings has a discrete rotational symmetry of at least an order eight.

14. The magnet array according to claim 1, and comprising one or more additional arrays of magnet rings, wherein the magnet rings in the additional arrays are coaxial with respective longitudinal axes that are set at respective angles from the longitudinal axis.

15. A method for producing a magnet array, the method comprising:

positioning multiple magnet rings along a longitudinal axis and coaxially with the longitudinal axis, wherein at least two of the magnet rings comprise mixed-phase magnet rings that are phase-dissimilar, and wherein the magnet rings are arranged with reflectional asymmetry with respect to the longitudinal axis, the multiple magnet rings configured to jointly generate a magnetic field along a direction parallel to the longitudinal axis of at least a given level of uniformity inside a predefined inner volume; and fixedly holding the multiple magnet rings in place using a frame.

16. The method according to claim 15, wherein two of the at least two mixed-phase magnet rings contain only a single permanent magnetic phase with a magnetization vector in a direction different by more than 45 degrees from one another.

17. The method according to claim 15, wherein each magnet ring has a rotational symmetry with respect to an in-plane rotation of the magnet ring around the longitudinal axis.

18. The method according to claim 15, wherein at least one of the magnet rings encircles the predefined inner volume, and wherein a minimal inner radius of the magnet rings positioned on one side of a center of the inner volume along the longitudinal axis is different from the minimal inner radius of the magnet rings positioned on the other side of the center of inner volume.

19. The method according to claim 15, wherein the inner volume is an ellipsoid of revolution around the longitudinal axis.

20. The method according to claim 15, wherein a given magnet ring is made of one of a single solid element and an assembly of discrete magnet segments.

21. The method according to claim 20, wherein the magnet ring is pre-magnetized with a respective magnetization direction that maximizes uniformity of the magnetic field inside the inner volume.

22. The method according to claim 20, wherein the magnet ring is pre-magnetized with a respective magnetization direction that minimizes a fringe field outside the magnet array.

23. The method according to claim 20, wherein the discrete magnet segments are electrically insulated from each other.

24. The method according to claim 22, wherein each of the discrete magnet segments has a shape that is one of a shape of sphere, a cylinder, an ellipsoid and a polygonal prism.

25. The method according to claim 22, wherein the discrete magnet segments are separated of each other by at least one non-magnetic element comprising a solid, gas or liquid.

26. The method according to claim 15, wherein each of the magnet rings has a shape comprising one of an ellipse, a circle and a polygon.

27. The method according to claim 15, wherein each of the mixed phase rings has a discrete rotational symmetry of at least an order eight.

28. The method according to claim 15, and comprising positioning one or more additional arrays of magnet rings, wherein the magnet rings in the additional arrays are coaxial with respective longitudinal axes that are set at respective angles from the longitudinal axis.

* * * * *